United States Patent [19]

Leone-Bay et al.

[11] Patent Number: 5,541,155

[45] Date of Patent: Jul. 30, 1996

[54] ACIDS AND ACID SALTS AND THEIR USE IN DELIVERY SYSTEMS

[75] Inventors: Andrea Leone-Bay, Ridgefield, Conn.; Noemi Santiago, Hawthorne, N.Y.

[73] Assignee: Emisphere Technologies, Inc., Hawthorne, N.Y.

[21] Appl. No.: 231,623

[22] Filed: Apr. 22, 1994

[51] Int. Cl.$^6$ .................. A61K 31/725; A61K 38/02; A61K 47/12

[52] U.S. Cl. .................. 514/2; 514/11; 514/12; 514/21; 514/56; 514/557; 514/784

[58] Field of Search ................. ; 514/784, 557, 514/570, 573, 574, 2, 11, 12, 21, 56, 3, 23, 54; 424/85.2, 85.4, 130.1, 184.1; A61K 47/12, 31/20, 31/19

[56] References Cited

U.S. PATENT DOCUMENTS

| | | | |
|---|---|---|---|
| Re. 24,899 | 11/1960 | Green | 514/784 |
| 2,671,451 | 3/1954 | Bolger | 604/288 |
| 2,862,918 | 12/1958 | Meyer et al. | 530/378 |
| 2,868,740 | 1/1959 | Luce | 527/202 |
| 2,971,916 | 2/1961 | Schleicher et al. | 252/62.53 |
| 3,016,308 | 1/1962 | Macaulay | 503/200 |
| 3,052,655 | 9/1962 | Fox et al. | 530/350 |
| 3,057,344 | 10/1962 | Abella et al. | 128/769 |
| 3,076,790 | 2/1963 | Fox et al. | 530/409 |
| 3,170,802 | 2/1965 | Fukushima | 426/46 |
| 3,190,837 | 6/1965 | Brynko et al. | 427/213.33 |
| 3,474,777 | 10/1969 | Figge et al. | 424/1.29 |
| 3,491,093 | 1/1970 | Pachter et al. | 544/144 |
| 3,565,559 | 2/1971 | Sato | 424/492 |
| 3,567,650 | 3/1971 | Bakan | 427/213.32 |
| 3,574,832 | 4/1971 | Engel et al. | 514/56 |
| 3,576,758 | 4/1971 | Emrick | 424/497 |
| 3,725,113 | 4/1973 | Chang | 424/493 |
| 3,748,277 | 7/1973 | Wagner | 252/316 |
| 3,794,561 | 2/1974 | Matsukawa et al. | 435/68.1 |
| 3,795,739 | 3/1974 | Birkmayer et al. | 514/419 |
| 3,822,348 | 7/1974 | Higashi et al. | 424/569 |
| 3,849,550 | 11/1974 | Teitelbaum et al. | 424/78.29 |
| 3,937,668 | 2/1976 | Zolle | 424/1.29 |
| 3,939,253 | 2/1976 | Bodor et al. | 514/547 |
| 3,956,172 | 5/1976 | Saeki et al. | 264/4.3 |
| 3,962,416 | 6/1976 | Katzen | 424/493 |
| 3,976,773 | 8/1976 | Curran | 424/250 |
| 4,035,507 | 7/1977 | Bodor et al. | 514/533 |
| 4,048,268 | 9/1977 | Ludwig | 264/15 |
| 4,061,466 | 12/1977 | Sjoholm et al. | 436/535 |
| 4,117,801 | 10/1978 | Dannelly et al. | 118/20 |
| 4,147,767 | 4/1979 | Yapel, Jr. | 424/499 |
| 4,183,849 | 1/1980 | Hansen et al. | 530/305 |
| 4,199,561 | 4/1980 | Roth et al. | 424/489 |
| 4,217,370 | 8/1980 | Rawlings et al. | 426/98 |
| 4,272,506 | 6/1981 | Schwarzberg | 436/512 |
| 4,289,759 | 9/1981 | Heavner et al. | 544/385 |
| 4,345,588 | 8/1982 | Widder et al. | 600/12 |
| 4,348,384 | 9/1982 | Horikoshi et al. | 424/450 |
| 4,351,337 | 9/1982 | Sidman | 424/425 |
| 4,352,883 | 10/1982 | Lim | 435/178 |
| 4,357,259 | 11/1982 | Senyei et al. | 264/4.3 |
| 4,388,304 | 6/1983 | Nyeki et al. | 514/16 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/DIG. 15 |
| 4,446,138 | 5/1984 | Pack | 514/235.2 |
| 4,450,150 | 5/1984 | Sidman | 424/424 |
| 4,460,563 | 7/1984 | Calanchi | 424/494 |
| 4,462,839 | 7/1984 | McGinley et al. | 106/198 |
| 4,462,991 | 7/1984 | Higuchi et al. | 514/784 |
| 4,473,620 | 9/1984 | Wu et al. | 428/402.24 |
| 4,483,807 | 11/1984 | Asano | 264/22 |
| 4,492,684 | 1/1985 | Goosen et al. | 424/486 |
| 4,518,433 | 5/1985 | McGinley et al. | 106/180 |
| 4,590,265 | 5/1986 | Bogan et al. | 536/63 |
| 4,608,278 | 8/1986 | Frank et al. | 514/962 |
| 4,613,500 | 9/1986 | Suzuki et al. | 514/2 |
| 4,647,455 | 3/1987 | De Bold | 514/21 |
| 4,666,641 | 5/1987 | Fickat et al. | 424/491 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,708,952 | 11/1987 | Salatinjants | 514/574 |
| 4,745,161 | 5/1988 | Saudek et al. | 525/420 |
| 4,753,804 | 6/1988 | Iaccheri et al. | 424/491 |
| 4,757,007 | 7/1988 | Satoh | 530/378 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |

- ● - Cyclohexanepropanoic acid/salt carrier
- ■ - Cyclohexanecarboxylic acid

| | | | |
|---|---|---|---|
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 514/563 |
| 4,886,663 | 12/1989 | Houghten | 530/327 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/2 |
| 4,919,939 | 4/1990 | Baker | 424/493 |
| 4,925,673 | 5/1990 | Steiner | 424/455 |
| 4,963,364 | 10/1990 | Fox et al. | 424/491 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,039,481 | 8/1991 | Pacifici et al. | 422/5 |
| 5,055,300 | 10/1991 | Gupta | 424/409 |
| 5,066,487 | 11/1991 | Morelle et al. | 556/181 |
| 5,067,961 | 11/1991 | Kelman et al. | 623/5 |
| 5,069,936 | 12/1991 | Yen | 424/484 |
| 5,077,278 | 12/1991 | Hafner et al. | 536/7.1 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/426 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 514/134 |
| 5,204,099 | 4/1993 | Barbier et al. | 514/18 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 514/401 |
| 5,250,236 | 10/1993 | Gasco | 264/4.4 |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,389,379 | 2/1995 | Dirix et al. | 424/451 |

FOREIGN PATENT DOCUMENTS

| | | | |
|---|---|---|---|
| 1077842 | 5/1980 | Canada. | |
| 0000667A1 | 2/1979 | European Pat. Off.. | |
| 0036145A1 | 9/1981 | European Pat. Off. | A67K 31/62 |
| 0105804 | 4/1984 | European Pat. Off.. | |
| 0130162A2 | 1/1985 | European Pat. Off.. | |
| 0342054A2 | 11/1989 | European Pat. Off.. | |
| 0342056A2 | 11/1989 | European Pat. Off.. | |
| 0365183 | 4/1990 | European Pat. Off.. | |
| 0366277 | 5/1990 | European Pat. Off.. | |
| 0448057 | 9/1991 | European Pat. Off.. | |
| 0459795 | 12/1991 | European Pat. Off.. | |
| 0467389 | 1/1992 | European Pat. Off.. | |
| 490549 | 6/1992 | European Pat. Off. | A61K 47/12 |
| 517211 | 12/1992 | European Pat. Off. | A61K 47/12 |
| 0616799A1 | 9/1994 | European Pat. Off. | A61K 7/00 |
| 71258/2 | 12/1987 | Israel. | |
| 56-68612 | 6/1981 | Japan | 514/557 |
| 58-35111 | of 1983 | Japan | A61K 9/66 |
| 929401 | 6/1963 | United Kingdom. | |
| 1075952 | 7/1967 | United Kingdom. | |
| 1236885 | 6/1971 | United Kingdom. | |
| 1567763 | 5/1980 | United Kingdom. | |
| WO85/00110 | 1/1985 | WIPO. | |
| WO85/00105 | 1/1985 | WIPO. | |
| WO85/02772 | 7/1985 | WIPO. | |
| WO87/04076 | 7/1987 | WIPO. | |
| WO88/01213 | 2/1988 | WIPO. | |
| WO92/19263 | 12/1992 | WIPO | A61K 39/00 |
| WO93/18754 | 9/1993 | WIPO | A61K 9/16 |
| WO93/25583 | 12/1993 | WIPO | C07K 15/00 |
| WO94/14420 | 7/1994 | WIPO | A61K 9/16 |
| WO94/21234 | 9/1994 | WIPO | A61K 7/00 |
| WO94/18997 | 9/1994 | WIPO | A61K 37/00 |
| WO94/18950 | 9/1994 | WIPO | A61K 9/127 |
| WO94/24291 | 10/1994 | WIPO | A61K 39/015 |
| WO94/23702 | 10/1994 | WIPO | A61K 9/16 |
| WO94/23767 | 10/1994 | WIPO | A61L 9/16 |
| WO94/28878 | 12/1994 | WIPO | A61K 9/14 |
| WO95/11690 | 5/1995 | WIPO | A61K 37/00 |

OTHER PUBLICATIONS

Chemical Abstract 83: 184360k (1975).

Life Sciences, vol. 33 No. 1 issued 1983, Gelb et al, "Cycloamylose Complexation of Adamantane Derivatives", pp. 83–85.

Airaudo, C. B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . .", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S. W. et al. (1976) *BioSystems*, vol. 8, pp. 40–44.

Fox, S. W. et al., *Molecular Evolution and the Origin of Life*, Maxel Decker, New York (1977).

Fox, S. W. et al. (1968) *Biochim. Biophys. Acta*, vol. 160, pp. 246–249.

Fox, S. W. (1976) *Origins of Life*, vol. 7, pp. 49–68.

Fox, S. W. (1980) *Naturwissenschaften*, vol. 67, pp. 378–383.

Fox, S. W. et al. (1960) *Archives of Biochemistry and Biophysics*, vol. 86, pp. 281–285.

Fox, S. W. et al. (1974) *Origins of Life*, vol. 5, pp. 227–237.

Fox, S. W. (1984) *Origins of Life*, vol. 14, pp. 485–488.

Gol'dovskii, A. M. (1978) *Zhurnal Evolyutsionnoi Biokhimii i Fiziologii*, vol. 14(6), pp. 517–519.

Gurrieri, S. et al. (1973) *Thermochimica Acta*, vol. 7, pp. 231–239.

Harada, K. et al. (1979) *BioSystems*, vol. 11, pp. 47–53.

Harada et al., (1960) *Archives of Biochemistry and Biophysics*, vol. 86, pp. 274–280.

Hare (1970) *Etude Cenetique De La Polycondensation Thermique D'χ-Amino Acides*, vol. 45, pp. 330–339.

Heinrich, M. R. et al. (1969) *Archives of Biochemistry and Biophysics*, vol. 130, pp. 441–448.

Heinz, B. et al. (1981) *BioSystems*, vol. 14, pp. 33–40.

Hennon, G. et al. (1975) *Biochimie*, vol. 57, pp. 1395–1396.

Hsu, L. L. et al. (1976) *BioSystems*, vol. 8, pp. 89–101.

Hsu, L. L. et al. (1971) *Currents in Modern Biology*, vol. 4, pp. 12–25.

Ishima, Y. et al. (1981), *BioSystems*, vol. 14, pp. 243–251.

Jackson et al. (1991) "Pharmacological . . .", *J. Pharm. & Exp. Thera.*, vol. 261, No. 1, pp. 546–552.

Jungck, J. R. et al. (1973) *Naturwissenschaften*, vol. 60, pp. 425–427.

Kokufuta, E. et al. (1984) *BioSystems*, vol. 16, pp. 175–181.

Lacey, Jr., J. C. et al. (1979) *BioSystems*, vol. 11, pp. 9–17.

Lacey, Jr., J. C. et al. (1979) *BioSystems*, vol. 11, pp. 1–7.

Martinez Luque–Romero, M. et al. (1986) *BioSystems*, vol. 19, pp. 267–272.

Masinovsky, Z. et al. (1989) *BioSystems*, vol. 22, pp. 305–310.

Matsuno, K. (1982) *BioSystems*, vol. 15, pp. 1–11.

Matsuno, K. (1984) *BioSystems*, vol. 17, pp. 11–14.

Matsuno, K. (1981) *BioSystems*, vol. 14, pp. 163–170.

McAlhaney, W. W. et al. (1976) *BioSystems*, vol. 8, pp. 45–50.

Melius, P. et al. (1987) *BioSystems*, vol. 20, pp. 213–217.

Melius, P. et al. (1975) *Bioorganic Chemistry*, vol. 4, pp. 385–391.

Melius, P. (1979) *BioSytems*, vol. 11, pp. 125–132.

Miquel, J. et al. (1971) *Currents in Modern Biology*, vol. 3, pp. 299–306.

Nakashima, T. et al. (1980) *J. Mol. Evol.*, vol. 15, pp. 161–168.

Nakashima, T. et al. (1981) *BioSystems*, vol. 14, pp. 151–161.

Novak, V. J. A. (1984) *Origins of Life*, vol. 14, pp. 513–522.

Olafsson, P. G. et al. (1971) *Polymer Letters*, vol. 9, pp. 521–528.

Phillips, R. D. et al. (1974) *Int. J. Peptide Protein Res.*, vol. 6, pp. 309–319.

Przybylski, A. T. et al. (1982) *Die Naturwissenschaften*, vol. 69, pp. 561–563.

Przybylski, A. T. et al. (1984) *Applied Biochemistry and Biotechnology*, vol. 10, pp. 301–307.Przybylski, A. T. (1985) *BioSystems*, vol. 17, pp. 281–288.

Rohlfing, D. L. (1975) *Origins of Life*, vol. 6, pp. 203–209.

Rohlfing, D. L. (1970) *Science*, vol. 169, pp. 998–1000.

Rohlfing, D. L. (1967) *Archives of Biochemistry and Biophysics*, vol. 118, pp. 468–474.

Rohlfing, D. L. et al. *Catalytic Activities of Thermal Polyanhydro-α-Amino Acids*, pp. 373–418 (no date).

Rohlfing, D. L. et al. (1976) *BioSystems*, vol. 8, pp. 139–145.

Ryan, J. W. et al. (1973) *BioSystems*, vol. 5, pp. 115–118.

Saunders, M. A. et al. (1974) *BioSystems*, vol. 6, pp. 81–92.

Snyder, W. D. et al. (1975) *BioSystems*, vol. 7, pp. 222–229.

Sokol, P. E. (1974) *Journal of the American Oil Chemists'Society*, vol. 52, pp. 101–102.

Vaughan, G. et al. (1987) *BioSystems*, vol. 20, pp. 219–223.

Vol'kenshtein, M. V. (1989) *Molekulyarnaya Biologiya*, vol. 23(1), pp. 23–37.

Waehneldt, T. V. et al. (1968) *Biochim. Biophys. Acta*, vol. 160, pp. 239–245.

Williams et al. (1991) *J. Biol. Chem.*, vol. 266, No. 8, pp. 5182–5190.

Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1985) *Chemical Abstracts*, vol. No. 105(1), Abstract No. 12027p.

(1985) *Chemical Abstracts*, vol. No. 102(6), Abstract No. 50870d.

Chemical Abstract, vol. 80(5) Abst. No. 52392a (1974).

Bergeron, Raymond J., et al. (1994) "Macromolecular Self-Assembly for Diketopiperazine Tetrapeptides", *Journal of the American Chemical Society*, vol. 116, pp. 8479–8484.

Bergeron, Raymond J., et al. (1993) "A Comparative Study of the Iron-Clearing Properties of Desferrithiocin Analogues With Desferrioxamine B in a *Cebus* Monkey Model", *Blood*, vol. 81, No. 8, pp. 2166–2173.

Bergeron, Raymond J., et al. (1992) "A Comparison of the Iron-Clearing Properties of 1,2-Dimethyl-3-Hydroxypyrid-4-One, 1,2-Diethyl-3-Hydroxypyrid-4-One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 378–393 (no date).

Andriuoli, G., et al. (1990), *Haemostasis* 20 (suppl. 1): 154–158.

Caramazza, I., et al. (1991), *Thrombosis Research* 62:785–789.

Guarini, S., et al (1983), *Experimentia* 41:350–352.

Guarini, S., et al. (1985), *Pharmacological Research Communications* 17(8): 685–697.

Dal Pozzo, A., et al. (1989), *Thrombosis Research* 56:119–124.

Watterberg et al. (1988), *Pediatric Research*, vol. 23, No. 4, part 2, p. 570A, col. 1, abstract No. 2209.

Bernstein (1985), *Chest* 87(1):68S–73S.

Damge et al. (1988), *Diabetes* 37:246–251.

Amino, Y., et al., *Chem. Pharm. Bull.* 36(11):4426–4434 (1988).

Baughman, R. A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "IBC Rational Drug Design Conference", San Diego, Calif.—Dec. 1994.

Leone–Bay et al., Presented at "Winter Conference on Medicinal and Bioorganic Chemistry" Steamboat Springs, Colorado—Feb. 1995 "Microsphere Formation and Drug Delivery in a Series of Derivatized Amino Acids".

Santiago et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (October Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., p. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6th Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug-loaded Proteinoid Microsphere Formulations during Freeze-drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, "Immunotherapy with Monoclonal Antibodies. 1990.

Michael E. Osband et al., Immunology Today, vol. 11, No. 6 1990, pp. 93–95, "Problems in the investigational study and clinical use of cancer immunotherapy".

Tibtech Feb. 1993 vol. 11, pp. 42–44 "Therapeutic antibodies—the coming of age".

Thomas A. Waldmann, Articles Jun. 21, 1991, pp. 1657–1662, "Monoclonal Antibodies in Diagnosis and Therapy".

*Primary Examiner*—Jeffrey E. Russel
*Attorney, Agent, or Firm*—Darby & Darby, PC

[57] ABSTRACT

The present invention relates to a delivery system, and in particular to carboxylic acids for use as a delivery system of sensitive agents such as bioactive peptides. The carboxylic acids and salts can form non-covalent mixtures with biologically-active agents. These mixtures are suitable for oral administration of biologically active agents to animals.

7 Claims, 6 Drawing Sheets

ACIDS AND ACID SALTS AND THEIR USE IN DELIVERY SYSTEMS

The present invention relates to compositions suitable for drug delivery, and in particular to compositions in which carboxylic acids and salts are used as carriers for biologically-active agents, including, but not limited to, bioactive peptides and the like. The acids and salts can formnoncovalent mixtures with biologically-active agents and are suitable for oral administration to animals. Methods for the preparation and for the administration of such compositions are also disclosed.

BACKGROUND OF THE INVENTION

Conventional means for delivering biologically-active agents, including, but not limited to, pharmaceutical and therapeutic agents to animals often are severely limited by chemical and physical barriers imposed by the body. Oral delivery of many biologically-active agents would be the route of choice if not for the presence of chemical and physico-chemical barriers such as extreme and varying pH in the gastro-intestinal (GI) tract, exposure to powerful digestive enzymes, and impermeability of gastro-intestinal membranes to the active ingredient. Among the numerous pharmacological agents which are are not suitable for oral administration are biologically-active peptides such as calcitonin and insulin. Examples of other compounds which are affected by the physico-chemical barriers are polysaccharides mucopolysaccharides, including, but not limited to, heparin, heparinoids, antibiotics and other organic substrates. These agents are rapidly destroyed in the gastro-intestinal tract by acid hydrolysis, enzymes, or the like.

Prior methods for orally administering vulnerable pharmacological agents have relied on co-administration of adjuvants (e.g., resorcinols and non-ionic surfactants such as polyoxyethylene oleyl ether and n-hexadecyl polyethylene ether) to increase artificially the permeability of the intestinal walls; and on co-administration of enzymatic inhibitors (e.g., pancreatic trypsin inhibitor, diisopropylfluorophosphate (DFF) and trasylol) to avoid enzymatic degradation. Liposomes have also been described as drug delivery systems for insulin and heparin. See, for instance, U.S. Pat. No. 4,239,754; Patel et al. (1976) *FEBS Letters* Vol. 62, page 60; and Hashimoto et al. (1979) *Endocrinol. Japan,* Vol. 26, page 337. The broader use of the aforementioned methods, however, as drug delivery systems are precluded for reasons which include: (1) the use of toxic amounts of adjuvants or inhibitors; (2) the lack of suitable low MW cargoes; (3) the poor stability inadequate shelf life of the systems; (4) difficulty in manufacturing; and (5) the failure of the systems to protect the active ingredient; and (6) the failure of the systems to promote absorption of the active agent.

More recently, microspheres of artificial polymers or proteinoids of mixed amino acids have been described for delivery of pharmaceuticals. For example, U.S. Pat. No. 4,925,673 describes such microspheres as well as methods for their preparation and use. The proteinoid microspheres of the '673 patent are useful for encapsulating a number of active agents.

There is a need in the art for a simple and inexpensive delivery system which is easily prepared and which can deliver a broad range of biologically-active agents.

SUMMARY OF THE INVENTION

Compositions for orally delivering biologically-active agents incorporating acids and acid salts as carriers are provided.

A composition comprising;
(A) at least one biologically-active agent; and
(B) (a) a compound having the formula:

$$R-CO_2H$$

wherein R is $C_1$ to $C_{24}$ alkyl, $C_2$ to $C_{24}$ alkenyl, $C_3$ to $C_{10}$ cycloalkyl, $C_3$ to $C_4$ cycloalkenyl, phenyl, naphthyl, ($C_1$ to $C_{10}$ alkyl) phenyl, ($C_2$ to $C_{10}$ alkenyl) phenyl, ($C_1$ to $C_{10}$ alkyl) naphthyl, ($C_2$ to $C_{10}$ alkenyl)naphthyl, phenyl ($C_1$ to $C_{10}$ alkyl), phenyl ($C_2$ to $C_{10}$ alkenyl), naphthyl $C_1$ to $C_{10}$ alkyl) and naphthyl ($C_2$ to $C_{10}$ alkenyl);

R being optionally substituted with $C_1$ to $C_{10}$ alkyl, $C_2$ to $C_{10}$ alkenyl, $C_1$ to $C_4$ alkoxy, —OH, —SH, —$CO_2^{R1}$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, $C_1$ to $C_{10}$ alk) aryl, aral $C_1$ to $C_{10}$) alkyl, or any combination thereof;

R being optionally interrupted by oxygen, nitrogen, sulfur, or any combination thereof; and
$R^1$ is hydrogen, $C_1$ to $C_4$ alkyl or $C_2$ to $C_4$ alkenyl;
(b) a salt thereof; or
(c) a combination of (a) and (b).

In an alternative embodiment, these compositions are used in oral dosage unit forms. The compositions or oral dosage unit forms be orally administrated to animals.

DETAILED DESCRIPTION OF THE INVENTION

Carboxylic acids and salts of carboxylic acids may be used as carriers to deliver biologically-active agents, such as peptides, mucopolysaccharides, carbohydrates, lipids and pesticides. These carriers are particularly useful in facilitating the delivery of orally sensitive biologically-active agents. For example, hormones such as calcitonin, insulin and polysaccharides such as heparin, are not considered orally administrable for various reasons. Insulin, for example, is sensitive to the denaturing conditions of the gastrointestinal (GI) tract. Also, heparin, by virtue of its charge and hydrophilic nature, is not readily absorbed from the gastro-intestinal tract.

The compositions of the subject invention are useful for administering biologically-active agents to any animals such as birds; mammals, such as primates and particularly humans; and insects.

The present invention, in several embodiments, uses readily available and inexpensive starting materials and provides a cost-effective method for preparing and isolating acids or salts thereof. The method is simple to perform and is amenable to industrial scale-up for commercial production.

Biologically-active agents suitable for use with carriers disclosed herein include, but are not limited to, peptides, and particularly small peptide hormones, which by themselves pass slowly or not at all through the gastro-intestinal mucosa and/or are susceptible to chemical cleavage by acids and enzymes in the gastrointestinal tract; polysaccharides and particularly mixtures of mucopolysaccharides, carbohydrates; lipids; or any combination thereof. Examples include, but are not limited to, human growth hormone; bovine growth hormone; growth hormone releasing hormone; interferons; interleukin-I; insulin; heparin, and particularly low molecular weight heparin; calcitonin; erythropoietin; atrial naturetic factor; antigens; monoclonal antibodies; somatostatin; adrenocorticotropin; gonadotropin releasing hormone; oxytocin; vasopressin; vancomycin; cromylyn sodium; desferrioxamine (DFO); or any combination thereof.

The carboxylic acids of the present invention have the formula:

wherein R is $C_1$ to $C_{24}$ alkyl, $C_2$ to $C_{24}$ alkenyl, $C_3$ to $C_{10}$ cycloalkyl, $C_3$ to $C_{10}$ cycloalkenyl, phenyl, naphthyl, $C_1$ to $C_{10}$ alkyl)phenyl, ($C_2$ to $C_{10}$ alkenyl)phenyl, $C_1$ to $C_{10}$ alkyl)naphthyl, ($C_2$ to $C_{10}$ alkenyl)naphthyl, phenyl($C_1$ to $C_{10}$ alkyl), phenyl($C_2$ to $C_{10}$ alkenyl), naphthyl $C_1$ to $C_{10}$ alkyl) and naphthyl ($C_1$ to $C_{10}$ alkenyl);

R being optionally substituted with $C_1$ to $C_{10}$ alkyl, $C_2$ to $C_{10}$ alkenyl, $C_1$ to $C_4$ alkoxy, —OH, —SH, —$CO_2R^1$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, $C_1$ to $C_{10}$ alk) aryl, aral($C_1$ to $C_{10}$) alkyl, or any combination thereof;

R being optionally interrupted by oxygen, nitrogen, sulfur, or any combination thereof; and $R^1$ is hydrogen, $C_1$ to $C_4$ alkyl or $C_2$ to $C_4$ alkenyl.

The preferred carboxylic acids are cyclohexanecarboxylic acid, cyclopentanecarboxylic acid, cycloheptanecarboxylic acid, hexanoic acid, 3-cyclohexanepropanoic acid, methylcyclohexanecarboxylic acid, 1,2-cyclohexanedicarboxylic acid, 1,3-cyclohexanedicarboxylic acid, 1,4-cyclohexanedicarboxylic acid, 1-adamantanecarboxylic acid, phenylpropanoic acid, adipic acid, cyclohexanepentanoic acid, cyclohexanebutanoic acid, pentylcyclohexanoic acid, 2-cyclopentanehexanoic acid, cyclohexanebutanoic acid, and (4-methylphenyl) cyclohexane acetic acid.

Additionally the carriers of the present invention can be used to deliver other active agents such as pesticides and the like.

In one embodiment, acids and salts thereof may be used directly as a drug delivery carrier by simply mixing the acids or salts with the active ingredient prior to administration. The acids and salts of the invention are particularly useful for the oral administration of certain biologically-active agents, e.g., small peptide hormones, which, by themselves, do not pass or only pass slowly through the gastro-intestinal mucosa and/or are susceptible to chemical cleavage in the gastrointestinal tract.

The carboxylic acids and salts of the invention do not alter the physiological and biological properties of the active agent. The system is particularly advantageous for delivering chemical or biological agents which otherwise would be destroyed or rendered less effective by conditions encountered within the body of the animal to which it is administered, before the agent reaches its target zone and pharmacological agents which are poorly absorbed in the gastrointestinal tract. The target zones can vary depending upon the drug employed.

Typically, the compositions of the present invention are prepared by mixing an aqueous solution of the carrier with an aqueous solution of the active ingredient, just prior to administration. Alternatively, the carrier and biologically active ingredient can be admixed during the manufacturing process. The solutions may optionally contain additives such as phosphate buffer salts, citric acid, acetic acid, gelatin and gum acacia.

In practicing the invention, stabilizing additives may be incorporated into the carrier solution. With some drugs, the presence of such additives promotes the stability and dispersibility of the agent in solution.

The stabilizing additives may be employed at a concentration ranging between about 0.1 and 5 % (W/V), preferably about 0.5 % (W/V). Suitable, but non-limiting, examples of stabilizing additives include gum acacia, gelatin, methyl cellulose, polyethylene glycol, and polylysine. The preferred stabilizing additives are gum acacia, gelatin and methyl cellulose.

The amount of active agent in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically-active agent compositions or may contain a divided pharmacologically or biologically effective amount. The total effective amounts will be administered by cumulative units containing, in total, pharmacologically or biologically active amounts of biologically-active agent.

The total amount of biologically-active agent to be used can be determined by those skilled in the art. However, it has surprisingly been found that with certain biologically-active agents, such as calcitonin, the use of the presently disclosed carriers provides extremely efficient delivery. Therefore, lower amounts of biologically-active agent than those used in prior dosage unit forms or delivery systems can be administered to the subject, while still achieving the same blood levels and therapeutic effects.

The amount of carrier in the present composition is a delivery effective amount and can be determined for any particular carrier or biologically-active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral or by intraduodenal injection.

EXAMPLES

The invention will now be illustrated in the following non-limiting examples which are illustrative of the invention but are not intended to limit the scope of the invention.

EXAMPLE 1

General Procedure for the Preparation of Carboxylic Acid Sodium Salts

The carboxylic acid is stirred with a minimal volume of water at room temperature. The mixture is adjusted to pH 7–7.5 by the portionwise addition of 2N aqueous sodium hydroxide. The resulting clear solution is lyophilized to give the desired carboxylic acid sodium salt as a white powder in quantitative yield.

EXAMPLE 2

Preparation of Calcitonin Dosing Solution

Cyclohexanepropionic acid sodium salt (800 mg) was placed in a test tube. Distilled water (3 mL) was added. The mixture was stirred to effect solution and the pH was adjusted to between 7.0–7.6 with sodium hydroxide or hydrochloric acid. The volume of added acid or base was recorded. The total volume of the solution was brought to 4 mL by the addition of distilled water. Calcitonin (20 ug) was added to the solution. The final carrier concentration was 200 mg/mL and the final calcitonin concentration was 5 ug/mL.

A similar process was used to prepare all of the dosing solutions used in these carboxylic acid sodium salt experiments.

EXAMPLE 3

Oral Delivery of Calcitonin to Rats

Figure 1:
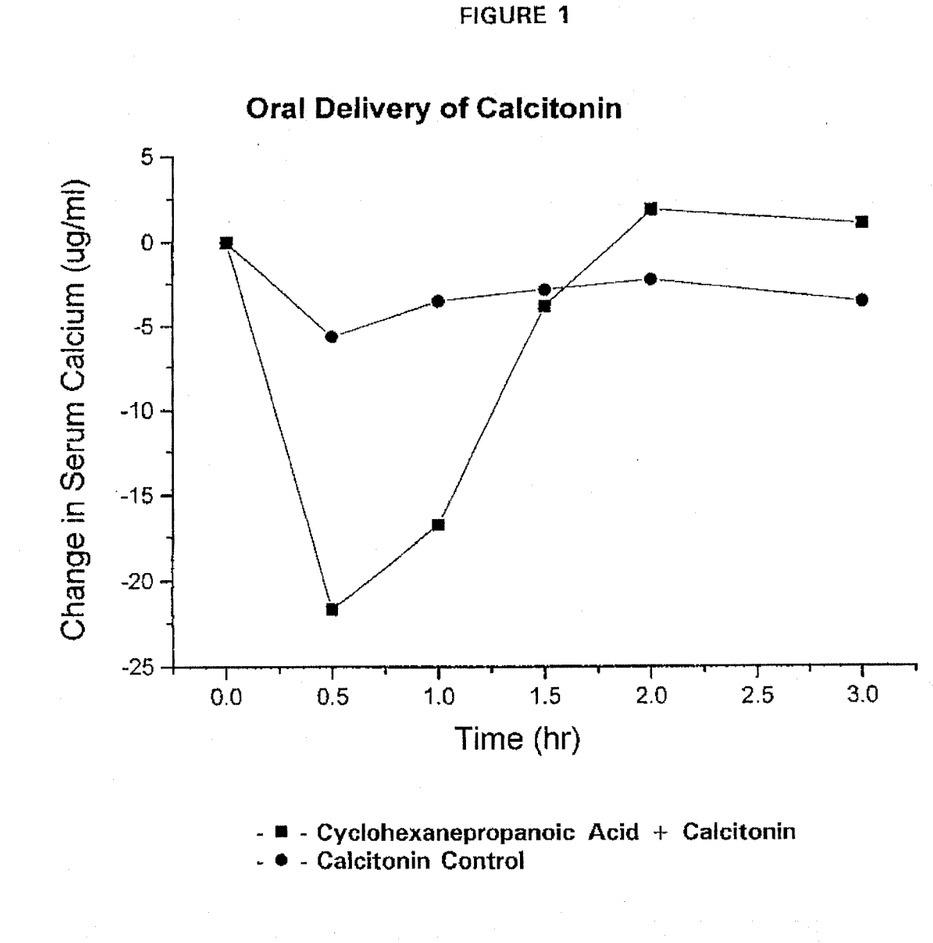
FIG. 1 is a graphic illustration of the results of oral garage testing in rats using calcitonin with cyclohexanepropanoic acid carrier.

For each sample, six fasted rats were anesthetized. The rats were administered, by oral gayage, one of the calcitonin/carrier dosages prepared as above. The calcitonin concentration in each sample was 1.5 ug/mL. Each rat was administered a dosage of two mL/kg. Blood samples were collected serially from the tail artery. Serum calcium was determined by testing with a Demand™ Calcium Kit (available from Sigma Chemical Company, St. Louis, Mo., USA). The results of the test are illustrated in FIG. 1.

EXAMPLE 4

Preparation of Heparin Dosing Solution

Cyclohexanepropionic acid sodiumsalt (900 mg) was added to 1,2-propanediol (4.5 mL) in a test tube and labelled Solution A. In another test tube, sodium heparin (300 mg) was added to a aqueous solution (4.5 mL) of 1.7N citric acid and 1.0% gum acacia and labelled Solution B. Both solutions were vortexed and heated in a water bath at about 37° C. for 15 minutes. Solution A was then poured into Solution B giving a mixture having a pH of about 4–5. The final carrier concentration was 100 mg/mL and the heparin concentration was 33.3 mg/mL. The pH of this solution could be adjusted to neutral by the addition of 50 mTrizma® hydrochloride buffer.

Following a similar procedure, a sample having cyclohexane carboxylic acid (900 mg) and sodium heparin (300 mg) was prepared. The solution had a heparin concentration of 33.3 mg/ml.

ORAL DELIVERY OF HEPARIN TO RATS

EXAMPLE 5

Figure 2:
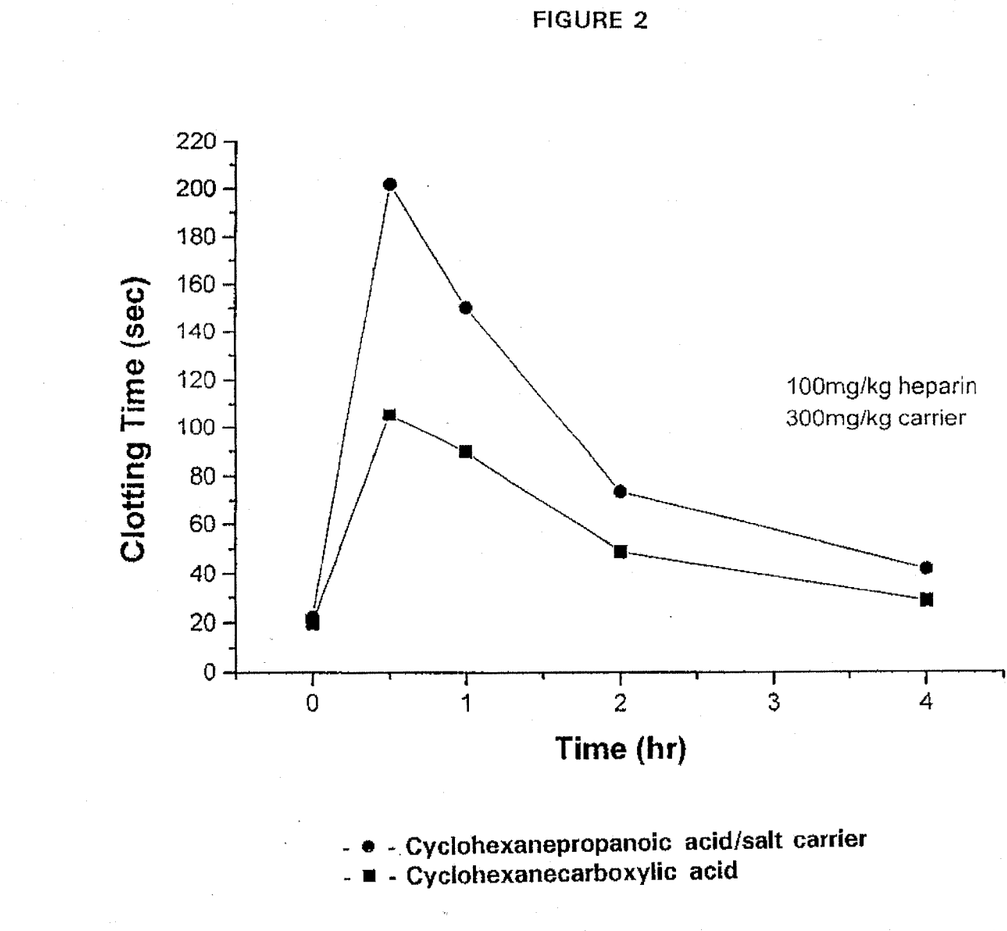
FIGS. 2 and 3 are graphic illustrations of the results of oral garage testing in rats using heparin with cyclohexanepropanoic acid and cyclohexane carboxylic acid carriers.

For each sample, five fasted rats were anesthetized. The rats were administered, by oral garage, one of the heparin/carrier dosages prepared in Example 4. The heparin activity in plasma was determined by use of the activated partial thromboplastin time (APTT; J. B. Henry, Clinical Diagnosis and Management by Laboratory Methods, Philadelphia: W. B. Saumders, 1979). The results of this test are illustrated in FIG. 2.

EXAMPLE 6

Figure 3:
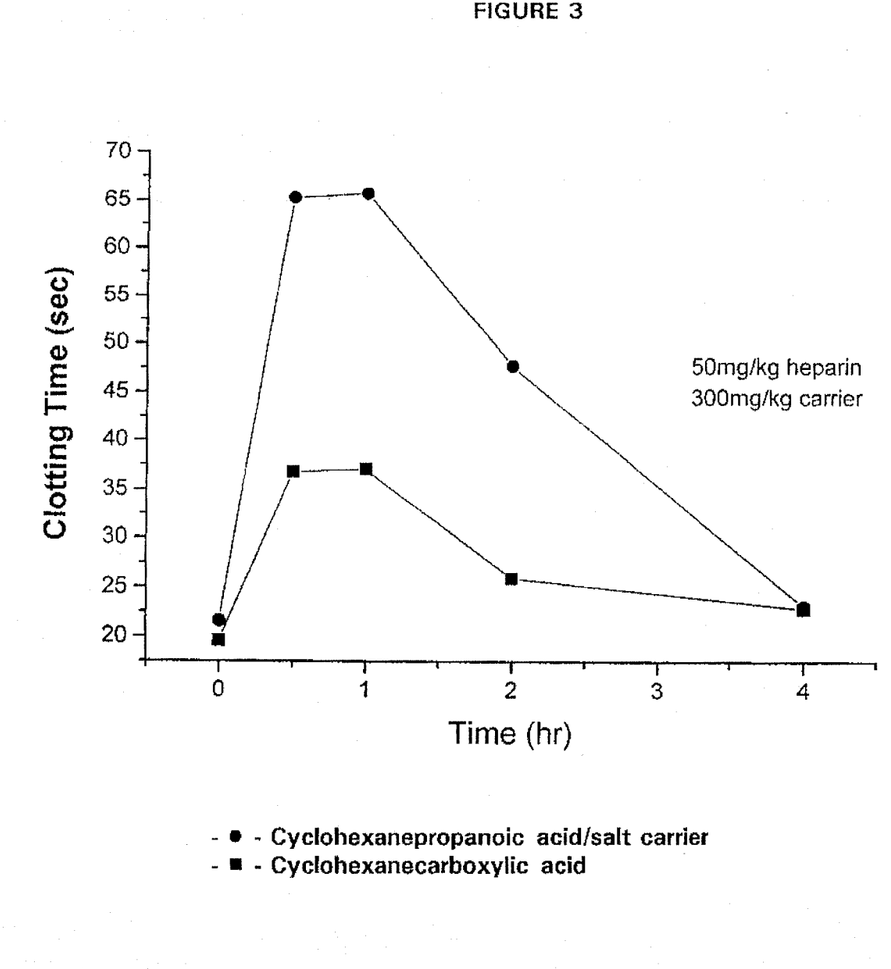

Two samples having 300 mg/kg of cyclohexanepropanoic acid and 50/mg/kg of Heparin and 300 mg/kg of cyclohexanecarboxylic acid and 50 mg/kg of heparin, respectively, were prepared. These were administered by oral garage to rats. The results are illustrated in FIG. 3.

EXAMPLE 7

Figure 4:
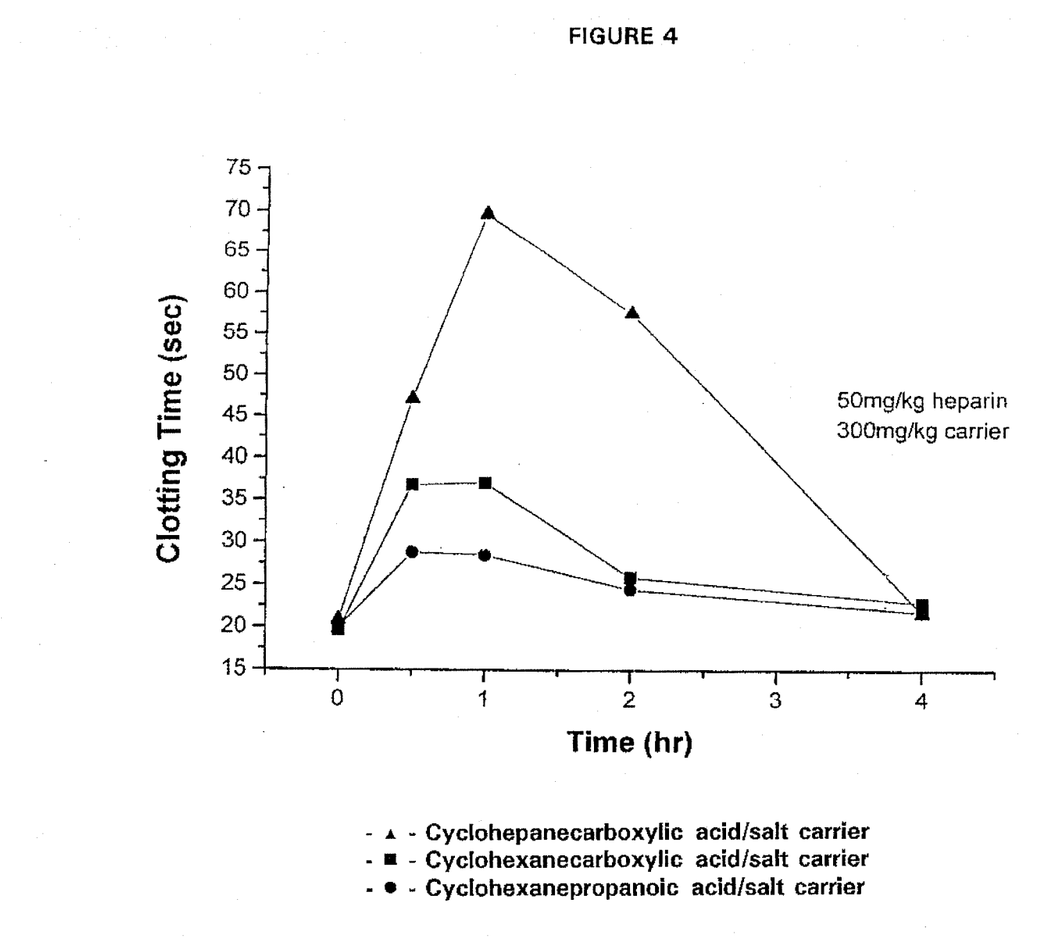
FIG. 4 is a graphic illustration of the results of oral garage testing in rats using heparin with cycloheptane-carboxylic acid, cyclohexanecarboxylic acid and cyclopentanecarboxylic acid carriers.

Three samples having 300 mg/kg of cycloheptanecarboxylic acid and 50 mg/kg of heparin and 300 mg/kg of cyclohexanecarboxylic acid and 50 mg/kg of heparin and 300 mg/kg of cyclopentanecarboxylic and 30 mg/kg of heparin, respectively, were prepared. These were administered by oral garage to rats. The results are illustrated in FIG. 4.

EXAMPLE 8

Figure 5:
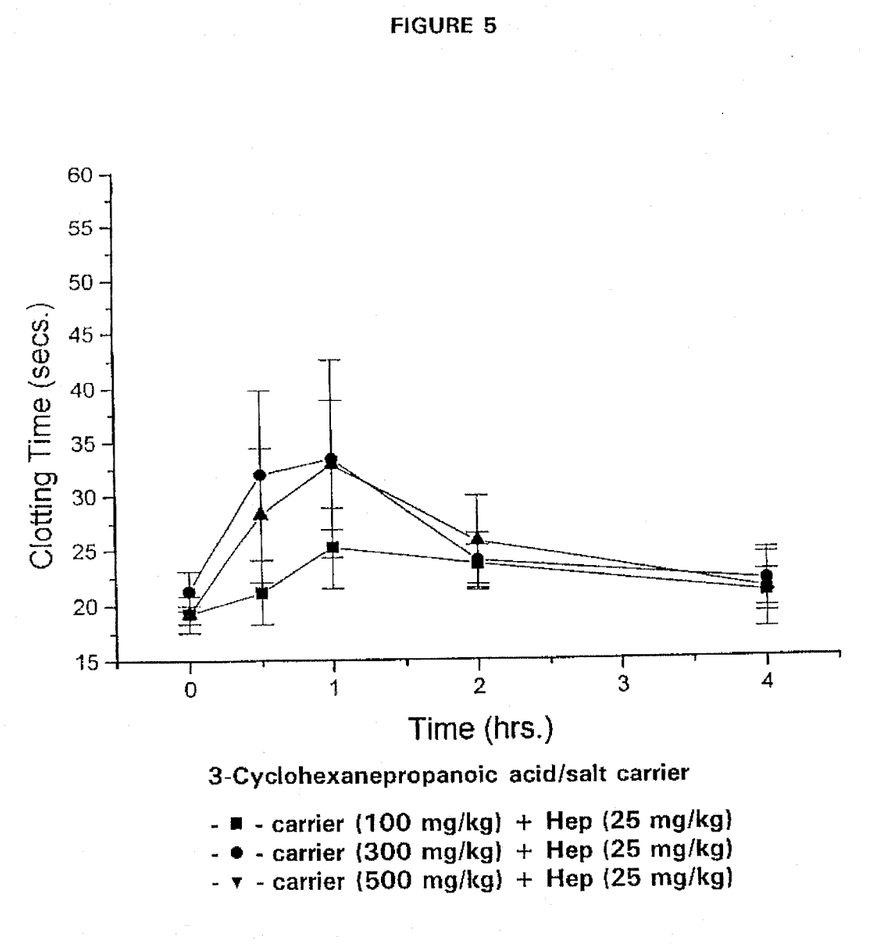
FIGS. 5 and 6 are graphic illustrations of the effects of varying the carrier loading and the cargo loading in oral garage testing in rats using heparin with cyclohexanepropanoic acid carrier.

Three samples having 100 mg/kg, 300 mg/kg and 500 mg/kg of cyclohexanepropanoic acid and 25 mg/kg of heparin, respectively, were prepared. These were administered by oral gavage to rats. The results are illustrated in FIG. 5.

EXAMPLE 9

Figure 6:
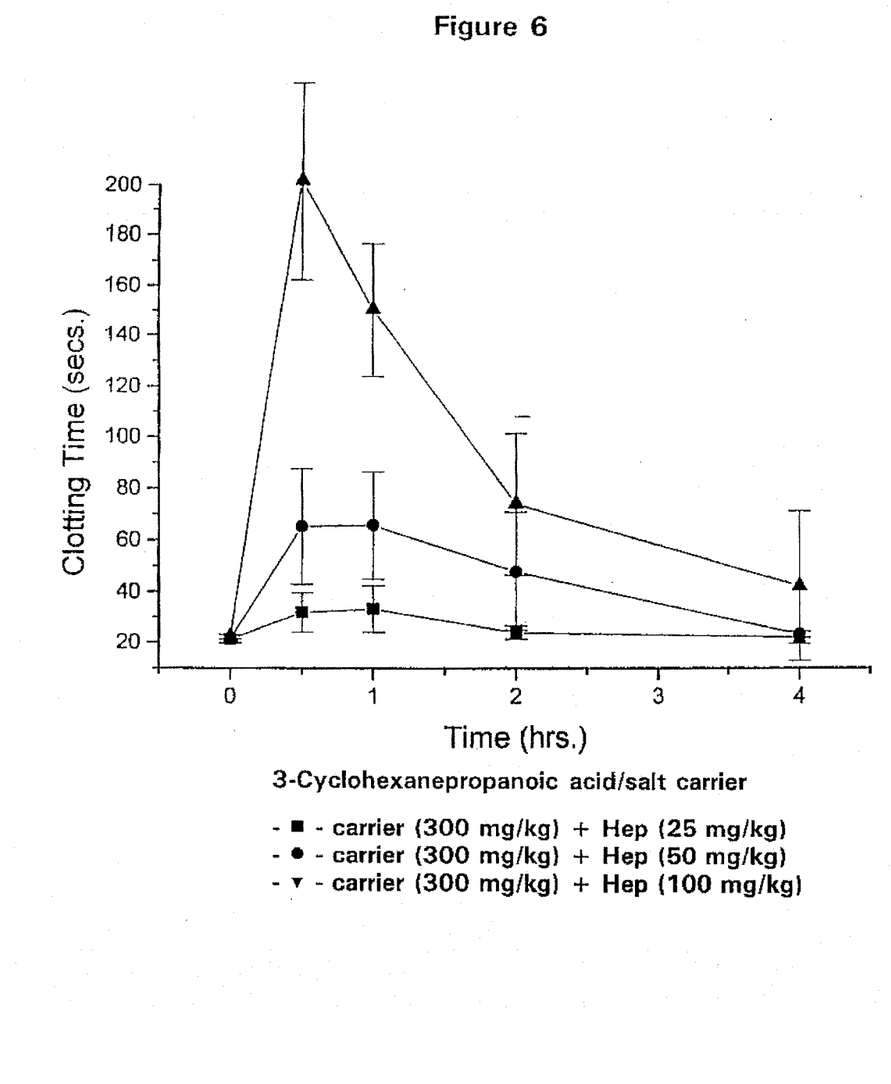

Three samples having 300 mg/kg cyclohexanepropanoic acid and 25 mg/kg, 50 mg/kg and 100 mg/kg of heparin, respectively, were prepared. These were administered by oral garage to rats. The results are illustrated in FIG. 6.

EXAMPLE 10

Further compositions of carriers with heparin were prepared and tested. The results are in Table 1.

TABLE 1

| HEPARIN CARRIERS | ACTIVITY (APTT × CONTROL) (mg/kg Carrier/mg/kg Hep) | | |
|---|---|---|---|
| | (300/100) | (300/50) | (300/25) |
| Cyclohexanecarboxylic acid | 5.31 | 1.70 | 1.31 |
| Cyclopentanecarboxylic acid | 4.58 | 1.44 | 1.05 |
| Cycloheptanecarboxylic acid | — | 1.31 | — |
| Hexanoic acid | 4.77 | 1.38 | — |
| 3-Cyclohexanepropanoic acid | 9.04 | 3.0 | 1.7 |
| Methylcyclohexanecarboxylic acid | 5.55 | — | 2.1 |
| 1,2-Cyclohexanedicarboxylic acid | 1.8 | — | — |
| 1,3-Cyclohexanedicarboxylic acid | 2.18 | — | — |
| 1,4-Cyclohexanedicarboxylic acid | 1.68 | — | — |
| 1-Adamantanecarboxylic acid | — | 2.43 | 1.00 |
| Phenylpropanoic acid | — | 2.48 | 1.2 |
| Cyclohexanepentanoic acid | — | 2.95 | 1.42 |
| Cyclohexanebutanoic acid | — | 4.2 | 1.3 |
| Pentylcyclohexanoic acid | — | 4.1 | — |

All patents, patent applications, literature publications and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A composition comprising; a compound having the formula:

; and a biologically-active agent selected from the group consisting of a peptide, a mucopolysaccharide, a carbohydrate, a lipid, a pesticide, cromolyn sodium, desferrioxamine (DFO), and a combination of the foregoing.

2. The composition according to claim 1, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), and any combination thereof.

3. The composition according to claim 2, wherein said biologically-active agent comprises an interferon, interleukin-II, insulin, heparin, calcitonin, oxytocin, vasopressin, cromolyn sodium, vancomycin, DFO or any combination thereof.

4. The composition according to claim 3, wherein said biologically-active agent is calcitonin.

5. The composition according to claim 3, wherein said biologically-active agent is heparin.

6. A composition for oral administration to an animal comprising 25 mg of heparin per kg of animal and 300 mg of cyclohexanecarboxylic acid per kg of animal.

7. A composition for oral administration to an animal comprising heparin and cyclohexanecarboxylic acid.

* * * * *